(12) United States Patent
Karlsson et al.

(10) Patent No.: US 9,005,160 B2
(45) Date of Patent: Apr. 14, 2015

(54) MEDICAMENT DELIVERY DEVICE

(75) Inventors: Martin Karlsson, Göteborg (SE); Nils Ronquist, Stockholm (SE)

(73) Assignee: SHL Group AB, Nacka Strand (SE)

(*) Notice: Subject to any disclaimer, the term of this patent is extended or adjusted under 35 U.S.C. 154(b) by 414 days.

(21) Appl. No.: 13/511,295

(22) PCT Filed: Oct. 15, 2010

(86) PCT No.: PCT/SE2010/051114
§ 371 (c)(1),
(2), (4) Date: May 22, 2012

(87) PCT Pub. No.: WO2011/053225
PCT Pub. Date: May 5, 2011

(65) Prior Publication Data
US 2012/0253274 A1 Oct. 4, 2012

Related U.S. Application Data

(60) Provisional application No. 61/254,792, filed on Oct. 26, 2009.

(30) Foreign Application Priority Data

Nov. 5, 2009 (SE) .................................... 0950827

(51) Int. Cl.
*A61M 37/00* (2006.01)
*A61M 5/24* (2006.01)
(Continued)

(52) U.S. Cl.
CPC .......... *A61M 5/2448* (2013.01); *A61M 5/2033* (2013.01); *A61M 5/3155* (2013.01); *A61M 5/3156* (2013.01); *A61M 5/31553* (2013.01); *A61M 5/31583* (2013.01)

(58) Field of Classification Search
USPC ..................................................... 604/82, 89
See application file for complete search history.

(56) References Cited

U.S. PATENT DOCUMENTS

| | | | | |
|---|---|---|---|---|
| 4,202,314 A | * | 5/1980 | Smirnov et al. | 604/138 |
| 4,755,169 A | * | 7/1988 | Sarnoff et al. | 604/511 |

(Continued)

FOREIGN PATENT DOCUMENTS

| | | |
|---|---|---|
| WO | 2008/122360 A2 | 10/2008 |
| WO | 2010/066796 A1 | 6/2010 |

OTHER PUBLICATIONS

Swedish Patent Office, Int'l Search Report in PCT/SE2010/051114, Feb. 10, 2011.

(Continued)

*Primary Examiner* — Nicholas Lucchesi
*Assistant Examiner* — Diva K Chander
(74) *Attorney, Agent, or Firm* — Piedmont Intellectual Property

(57) ABSTRACT

A medicament delivery device includes a distal housing part; a proximal housing part in which a multi-chamber medicament container is arranged, with the proximal housing part movable relative to the distal housing part for mixing substances in the container; a plunger rod arranged to act on a stopper in the container, where movement of the housing parts toward each other forces the stopper against the plunger rod for mixing the substances in the container; a drive force unit for forcing the plunger rod for subsequent delivery of medicament; an activation member slidable through the distal housing part and releasably connected to the drive force unit; and a guide shell one-way rotatable in the distal housing part with threads that cooperate with threads on the proximal housing part. The guide shell and plunger rod have guide members such that they are rotationally locked but slidable in relation to each other.

8 Claims, 6 Drawing Sheets

(51) Int. Cl.
*A61M 5/20* (2006.01)
*A61M 5/315* (2006.01)

(56) References Cited

U.S. PATENT DOCUMENTS

| | | | |
|---|---|---|---|
| 4,822,340 A * | 4/1989 | Kamstra | 604/135 |
| 4,874,381 A * | 10/1989 | Vetter | 604/191 |
| 4,968,299 A * | 11/1990 | Ahlstrand et al. | 604/90 |
| 6,793,646 B1 * | 9/2004 | Giambattista et al. | 604/90 |
| 8,092,420 B2 * | 1/2012 | Bendek et al. | 604/89 |
| 8,372,031 B2 * | 2/2013 | Elmen et al. | 604/89 |
| 8,403,883 B2 * | 3/2013 | Fayyaz et al. | 604/90 |
| 8,439,864 B2 * | 5/2013 | Galbraith et al. | 604/90 |
| 8,500,682 B2 * | 8/2013 | Cronenberg et al. | 604/90 |
| 8,529,503 B2 * | 9/2013 | Elmen et al. | 604/89 |
| 2009/0118669 A1 | 5/2009 | Bendek et al. | |
| 2010/0152672 A1 | 6/2010 | Raab | |
| 2012/0253274 A1 * | 10/2012 | Karlsson et al. | 604/89 |

OTHER PUBLICATIONS

Swedish Patent Office, Written Opinion in PCT/SE2010/051114, Feb. 10, 2011.

* cited by examiner

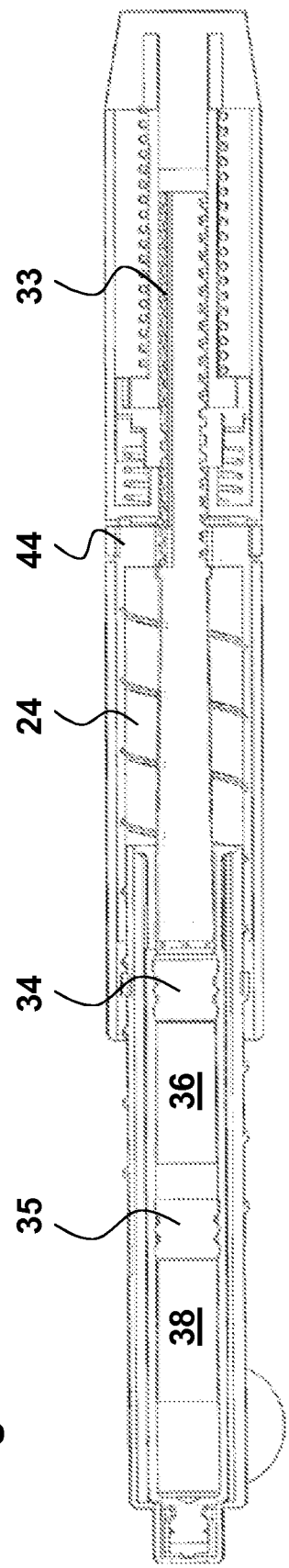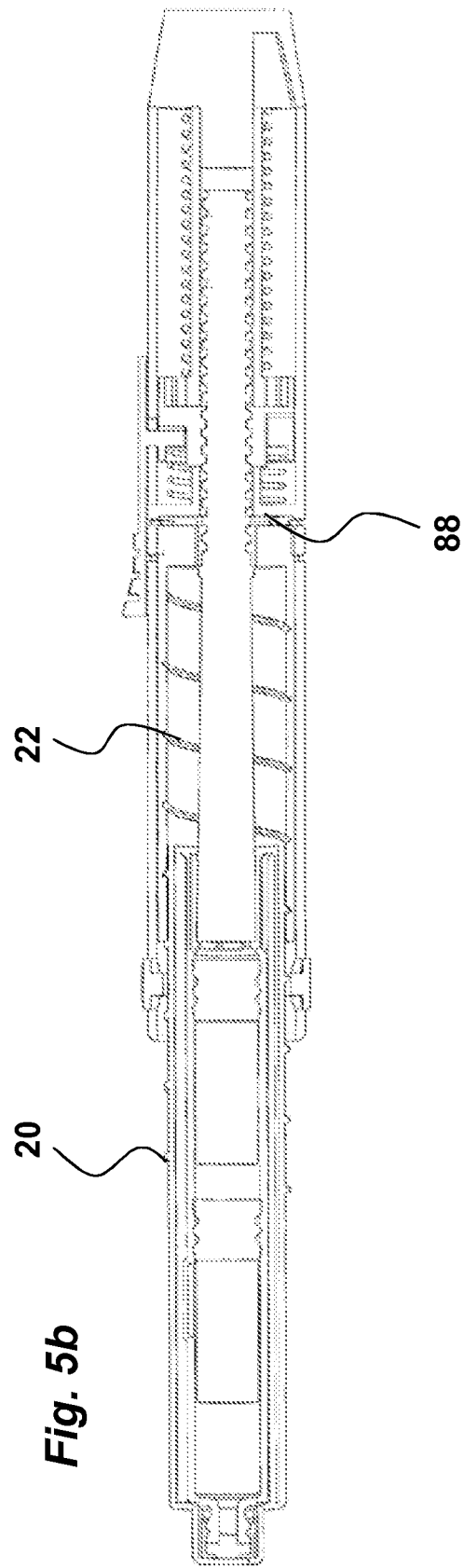

MEDICAMENT DELIVERY DEVICE

TECHNICAL AREA

The present invention relates to a medicament delivery device and in particular a reusable device capable of handling multi-chamber medicament containers.

BACKGROUND OF INVENTION

There are numerous devices for delivering medicament on the market and also patented where the medicament is arranged in a container, such as a syringe, cartridge and the like, and wherein the medicament is exposed to pressure when it is to be delivered. A very common design is a generally tubular compartment having a stopper in one end of the compartment and a delivery member attached to the opposite end of the compartment, such as e.g. a needle, a nozzle or the like member capable of delivering medicament to a patient.

In order to deliver a quantity of medicament, the stopper is exposed to pressure, i.e. pushed into the compartment by a plunger rod, which could be done manually by a finger, which is the case for simple handheld syringes, or by pressure means such as springs, which is common in automatic or semi-automatic injectors.

The plunger rods of many medicament delivery devices are threaded and cooperate with threaded nuts whereby either the plunger rod is rotated or the nut is rotated when advancing the plunger rod. For disposable medicament delivery devices this solution works very well because when the plunger rod has moved to its most forward position, the medicament container is empty and the medicament delivery device can be discarded. However, for reusable medicament delivery devices, there is a problem when using threaded plunger rods because they have to be threaded back to their original position.

This operation is not appreciated by most users, and may also lead to wrong handling of the device in that there could be an uncertainty as to how far the plunger rod should be threaded back. Further, there are a number of medicament delivery devices where the delivery mechanisms, and mechanisms associated with the delivery, do not permit a return of the plunger rod.

Further, the use of multi-chamber medicament containers is becoming more and more popular wherein the medicament in dry form is mixed with a diluent just prior the medicament delivery. This entails a further operation that may be performed in different ways. Document WO2007/115424 discloses a medicament delivery device for multi-chamber containers comprising two housing parts that are in threaded engagement. When the two housing parts are threaded together a plunger rod inside the housing parts acts on a distal stopper of the medicament container, whereby the dry medicament is mixed with the diluent. The device also discloses that a dose can be set and delivered, after which the device becomes locked in order to prevent misuse. The device can then be discarded. However the device of WO2007/115424 is neither intended for multiple doses nor for multiple containers.

BRIEF DESCRIPTION OF INVENTION

The aim of the present invention is to provide a multi-use medicament delivery device capable of handling multi-chamber medicament containers in a simple and reliable way.

This aim is obtained by a medicament delivery device characterised by the features of the independent patent claim. Preferable embodiments of the invention form the subject of the dependent patent claims.

According to a main aspect of the invention it is characterised by a medicament delivery device comprising a distal housing part; a proximal housing part into which a multi-chamber medicament container is arranged and wherein said proximal housing part is arranged to be movable in relation to said distal housing part for mixing at least two substances arranged inside said container; a plunger rod arranged to act on a distal stopper in said medicament container, wherein a relative movement of said housing parts towards each other forces said distal stopper against the plunger rod in a proximal direction for mixing at least two substances arranged inside said container; a drive force unit capable of forcing said plunger rod in the proximal direction for subsequent delivery of medicament from said medicament container; an activation member slidably arranged through said distal housing part and releasably connected to the drive force unit; wherein said device further comprises a guide shell one-way rotatable arranged in said distal housing part, wherein said guide shell is provided with threads arranged to cooperate with corresponding threads on said proximal housing, and wherein said guide shell and said plunger rod are arranged with guide members such that they are rotationally locked but slidable in relation to each other.

According to another aspect of the invention, the guide shell is arranged with a longitudinally extending ratchet on its distal outer circumferential surface, wherein said ratchet is arranged to cooperate with ledges provided on flexible tongues arranged on the distal housing part, and wherein the ratchet and the ledges are arranged such that the guide shell may only be rotated in one direction in relation to said distal housing part.

According to a further aspect of the invention it comprises a proximal housing part locking member attached to the distal housing part, wherein said locking member is provided with locking means arranged to engage with corresponding locking means on said proximal housing part when the housing parts have reached a certain relative position after mixing, and wherein, when the medicament container is to be replaced with another, the proximal housing part locking member is activated to release the engagement between said locking means, such that when a relative movement of said housing parts against each other also rotates said guide shell, whereby said plunger rod is moved in a distal direction to its initial position, and the proximal housing part is unscrewed from the distal housing part.

According to another aspect of the invention, said drive force unit comprises a drive nut in threaded engagement with said plunger rod and releasably connected to said activation member; a manually operated spring tensioning means comprising flexible locking tongues releasably connected to a ratchet of said drive nut for enabling rotational movement of said spring tensioning means only in one direction in relation to said drive nut; and a drive spring having one end connected to said spring tensioning means and a second end connected to the distal housing part; such that when said spring tensioning means is operated, said drive spring is locked in a tensioned state, and when said activation member is operated, said drive nut is released and thereby said drive spring is released from its tensioned state whereby said plunger rod is moved in the proximal direction for delivery of medicament.

Preferably said drive spring member is a torsion spring.

There are a number of advantages with the present invention. Due to the use of the guide shell and its interaction with the proximal housing part when a used medicament container is to replaced by a new, the plunger rod is moved to its initial position when the proximal housing part is screwed off the distal housing part, whereby the device is ready to receive the new medicament container without the need additional operations of moving the plunger rod. This facilitates the handling of the device.

Apart from that, the device according to the present invention provides a device capable of delivering a number of doses where the dose setting knob also acts as tensioner of the drive spring. This in turn means that the drive spring does not have to be in a pre-tensioned state before the device is used.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIGS. 5-6 are cross-sectional views of the device according to the present invention in different functional states.

DETAILED DESCRIPTION OF THE INVENTION

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

Figure 1:
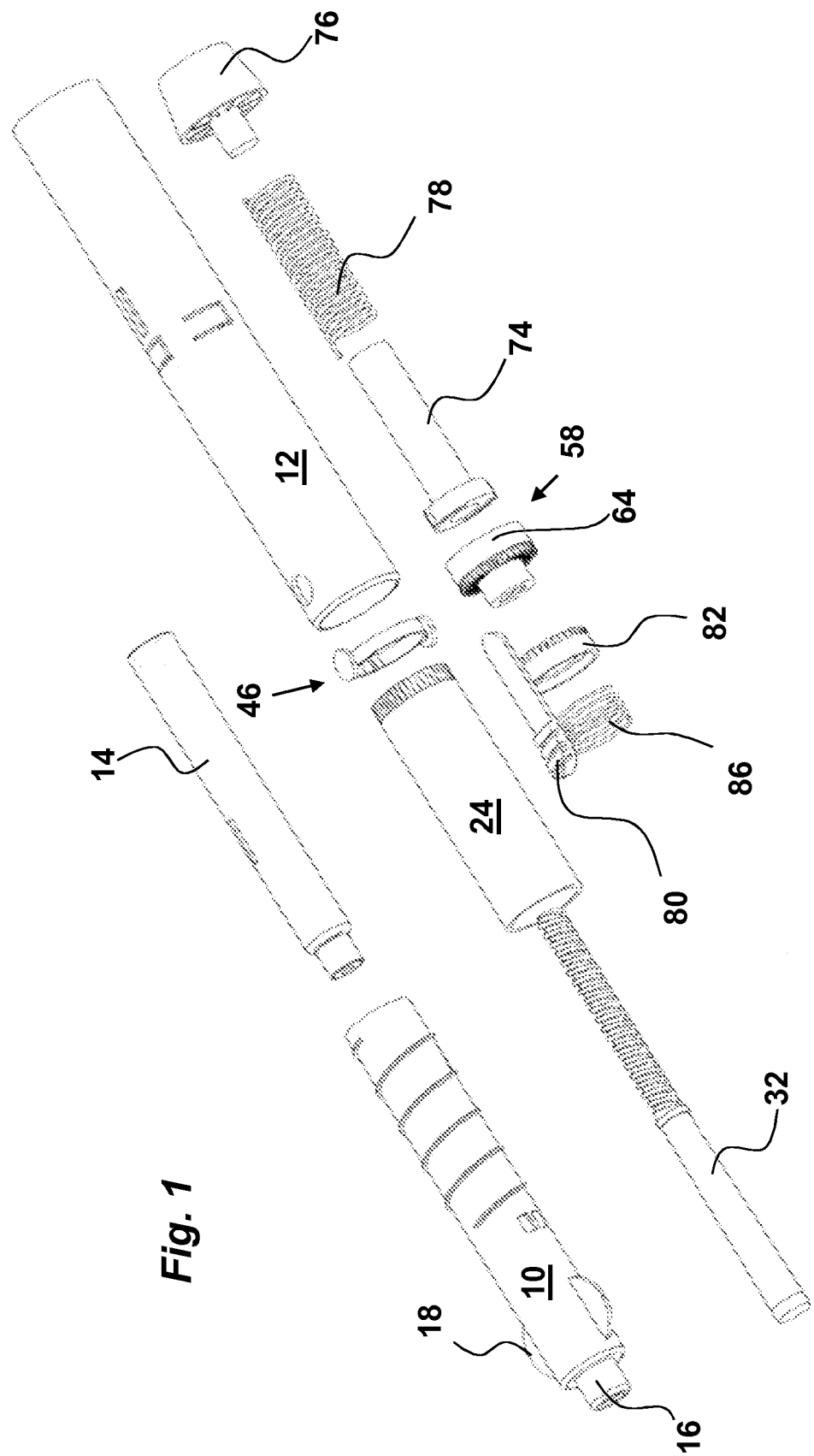
FIGS. 1-2 are exploded views of an embodiment of the present invention.

As seen in FIG. 1, the device according to the invention comprises a proximal housing part 10 and a distal housing part 12. It is however to be understood that the housing may be designed in many other ways. The proximal housing part is arranged as a medicament container holder which accommodates a multi-chamber medicament container 14. The proximal housing part is arranged to be movable in relation to said distal housing part for mixing at least two substances arranged inside said container. The proximal housing part is further arranged with a neck 16 at its proximal end for attaching a medicament delivery member such as an injection needle, a mouth piece a nozzle or the like. Further the proximal housing part is arranged with two handle members 18, the function of which will be described below. Also the outer surface of the proximal housing part is arranged with threads 20.

The device also comprises of a sleeve-like member, hereafter named guide shell 24 which is one-way rotatable arranged in said distal housing part. The threads 20 of the proximal housing part are arranged to cooperate with corresponding threads 22, FIG. 5b, arranged on an inner surface of a sleeve-like member, hereafter named guide shell 24. The distal end of the guide shell 24 is arranged with an end wall 26 having a central passage 28, FIG. 2. The central passage 28 is arranged with guide members 30 such as radially inwardly directed protrusions. A plunger rod 32 is arranged slidable in the central passage and is arranged with corresponding guide members 33 such as longitudinal grooves 33 into which the protrusions 30 fit, in order to provide a rotational lock between the plunger rod 32 and the guide shell 24. The proximal end of the plunger rod is arranged to be in contact with a distal stopper 34 inside the medicament container, FIG. 5a. A proximal stopper 35 is also arranged inside the medicament container; thereby forming two chambers 36, 38, inside the container 14 where one chamber 36 contains a first substance e.g. medicament in dry form and the other chamber 38 contains a second substance e.g. a diluent in liquid form, FIG. 5a. A relative movement of said housing parts 10, 12 towards each other forces said distal stopper against the plunger rod in a proximal direction for mixing the at least two substances arranged inside said container The guide shell 24 is arranged with a longitudinally extending ratchet 40 on its distal circumferential outer surface, FIG. 2, wherein said ratchet 40 is arranged to cooperate with ledges 44 provided on flexible tongues 42 arranged on the distal housing part 12, and wherein the ratchet and the ledges 44 are arranged such that the guide shell may only be rotated in one direction in relation to said distal housing part, FIG. 5a. Further a locking member 46, FIG. 3, is designed as a ring-shaped member 48 provided with two button-like members 50 arranged diametrically on the ring-shaped member 48. The two button-like members 50 are arranged to protrude through two diametrically arranged passages 52 on the distal housing part 12, FIG. 2. Further the ring-shaped member 48 is arranged with locking means 54 such as two diametrically positioned grooves, which are arranged to engage with corresponding locking means 56 such as two ribs on the outer surface of the proximal housing part, FIG. 3, when the housing parts have reached a certain relative position after mixing, and wherein, when the medicament container is to be replaced with another, the proximal housing part locking member is activated to release the engagement between said locking means 54, 56, such that when a relative movement of said housing parts 10, 12 against each other also rotates said guide shell, whereby said plunger rod is moved in a distal direction to its initial position, and the proximal housing part is unscrewed from the distal housing part.

Further, a drive force unit is arranged within said distal housing part and is interactively connected to the plunger, wherein said drive force unit is capable of forcing said plunger rod in the proximal direction for subsequent delivery of medicament from said medicament container. Further, an activation member 80 is slidably arranged through a slit on the circumferential surface of the distal housing part and is releasably connected to the drive force unit, as will be described below.

The drive force unit comprises a drive nut 58 which is in threaded engagement with said plunger rod 32 and which is releasably connected to said activation member, as will be described below; a manually operated spring tensioning means comprising flexible locking tongues, or arms, 72 which are releasably connected to a ratchet, or stop ledges, 70 of said drive nut for enabling rotational movement of said spring tensioning means only in one direction in relation to said drive nut, as will be described below; and a drive spring 78 having one end connected to said spring tensioning means and a second end connected to the distal housing part; such that when said spring tensioning means is operated, said drive spring is locked in a tensioned state, and when said activation member is operated, said drive nut is released and thereby said drive spring is released from its tensioned state whereby said plunger rod is moved in the proximal direction for delivery of medicament.

Figure 2:
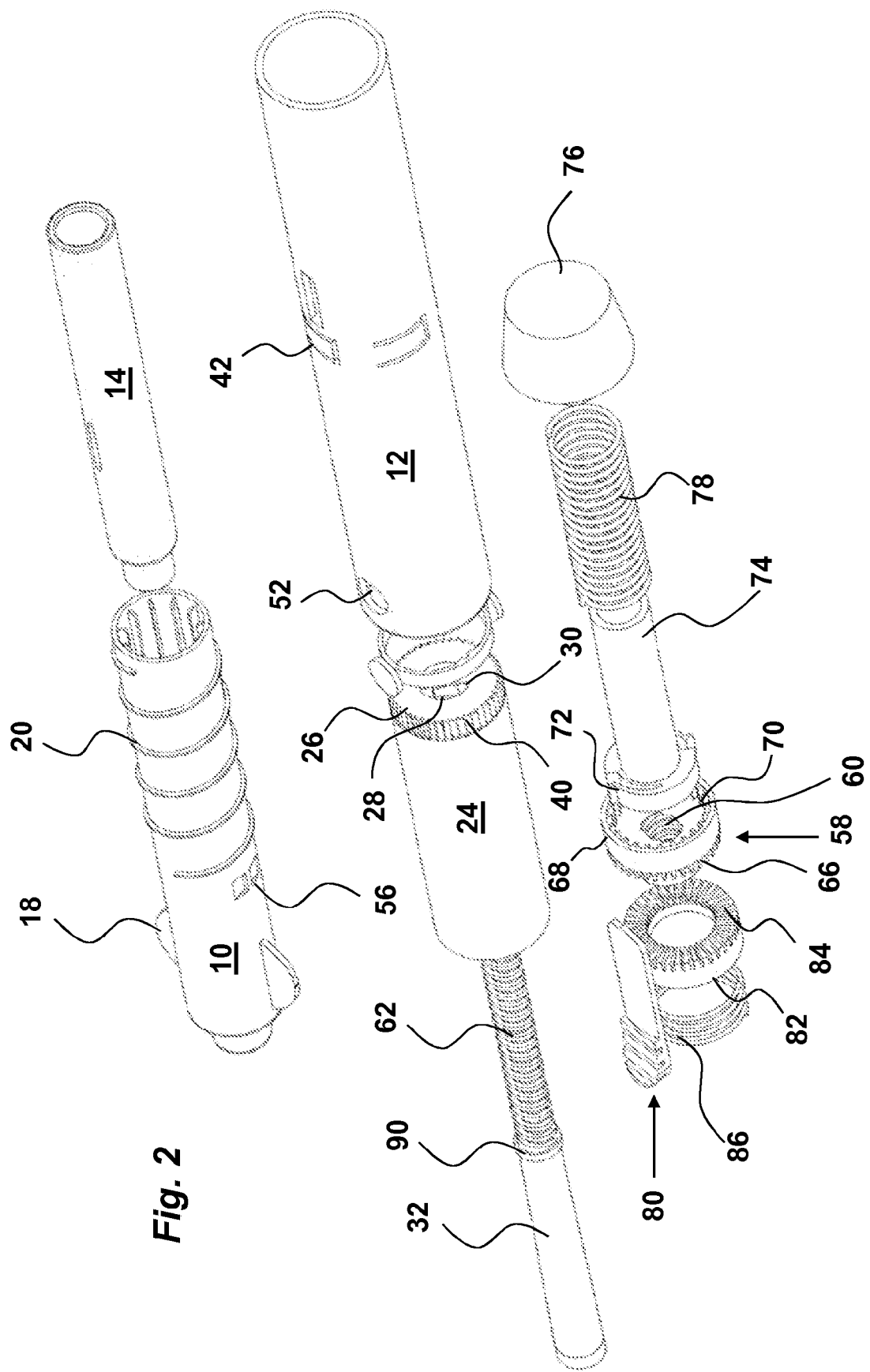
Figure 3:
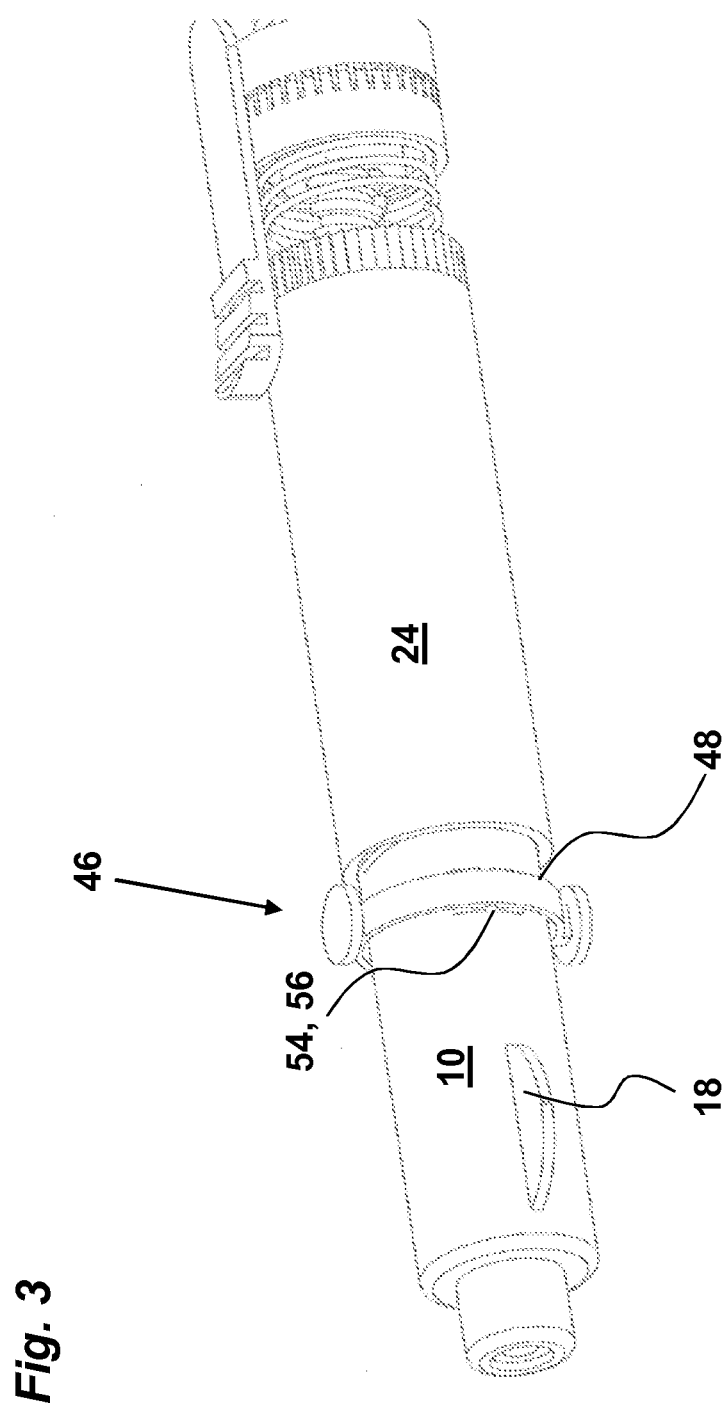
FIG. 3 is a detailed view of a proximal part of an embodiment of the present invention, with a distal housing part removed.
Figure 4:
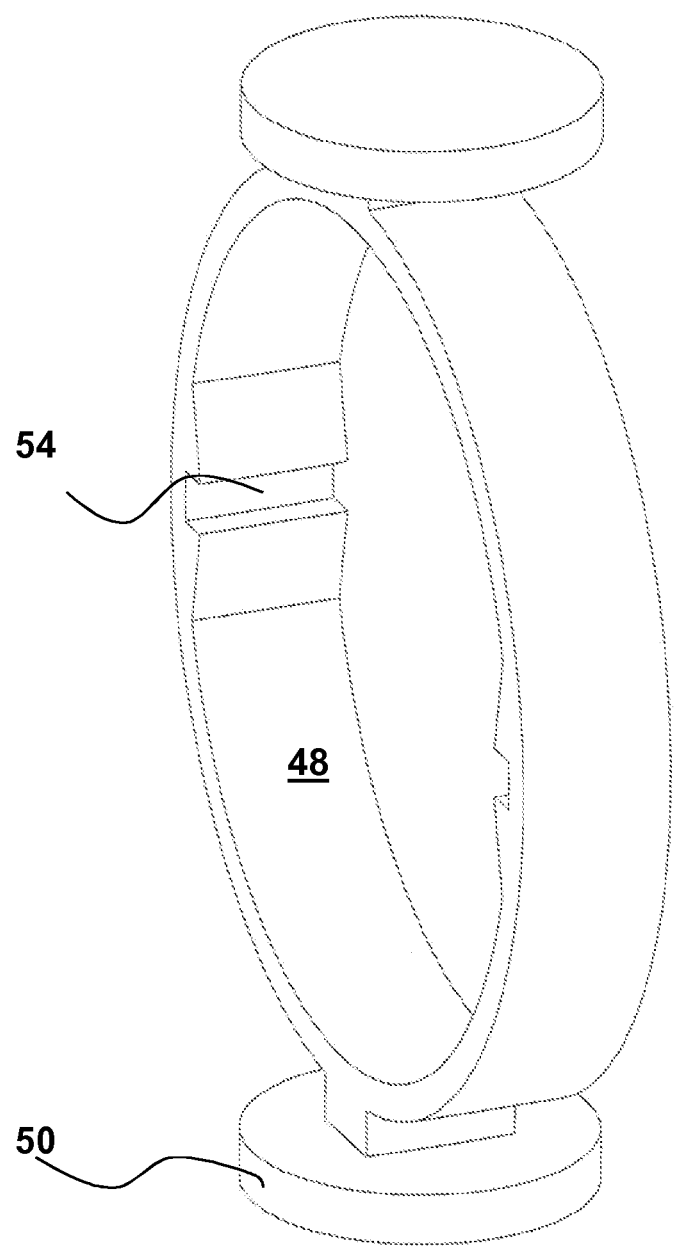
FIG. 4 is a detailed view of a component of the present invention.
Figure 6A:
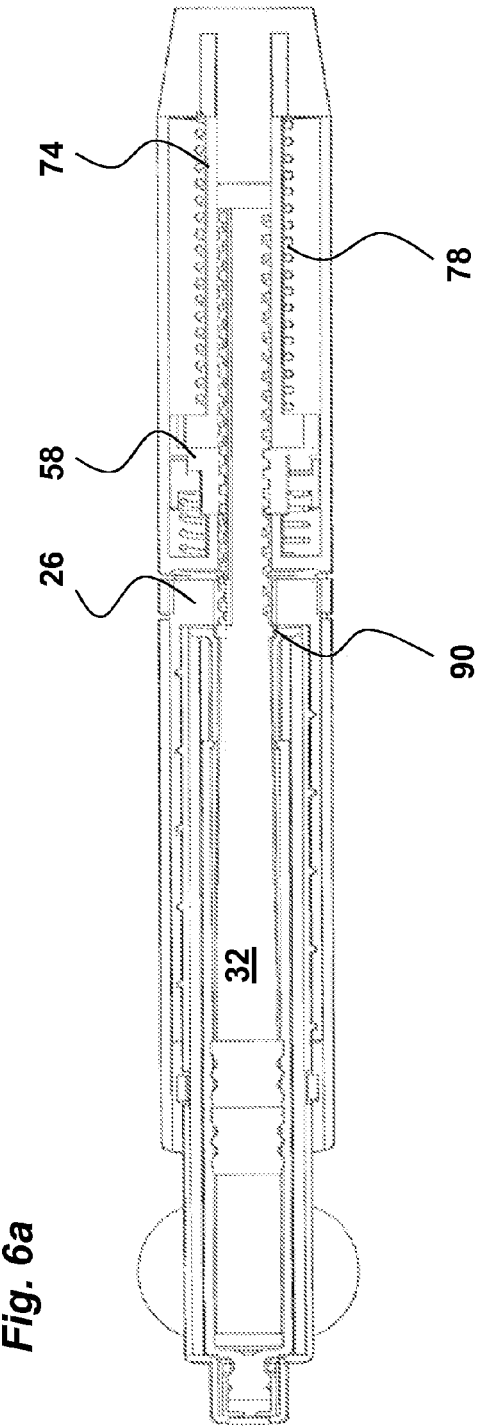
Figure 6B:
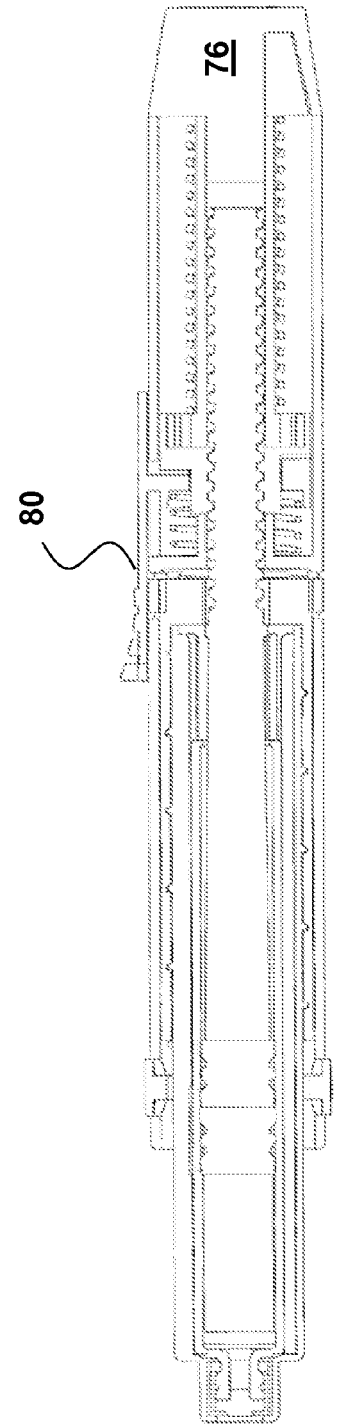

The plunger rod 32 is arranged inside the drive nut 58 where the inner surface of the drive nut 58 is provided with threads 60, FIG. 2, which cooperate with threads 62 on the outer surface of the plunger rod 32. The drive nut 58 is further arranged with an annular proximally directed ledge 64 having a number of teeth 66 around said ledge, the function of which will be described below. The distal end of the drive nut 58 is arranged with a ring-shaped part 68, where the inner circumferential surface of the ring is arranged with longitudinal stop ledges 70.

The manually operated spring tensioning means comprises a generally tubular drive member 74 and a dose setting knob 76. The stop ledges 70 of the drive nut cooperate with the flexible arms 72 arranged at the proximal end of the generally tubular drive member 74, FIG. 2. The distal end of the drive member 74 protrudes through the distal end of the distal housing part, where the dose setting knob 76 is attached, for rotating said drive member 74.

However, the stop ledges 70 and the flexible arms 72 are arranged such that the drive member 74 may only be rotated in one direction in relation to the drive nut 58, where the flexible arms 72 slide over the stop ledges 70. In the other direction, the ends of the flexible arms 72 abut the stop ledges 70, thereby blocking the rotation. The drive spring, which is a torsion drive spring, is coaxially arranged on the drive member 74 and comprises one end attached to the drive member 74 and a second end attached to a fixed part of the device, such as the distal housing part 12.

A predetermined dose of medicament is set by the use of the spring tensioning means, with the use of which the dose is increased by predetermined equally large dose increment steps. One predetermined dose increment step, corresponds to a clock-wise rotation of the dose setting knob 76 with one predetermined step, which predetermined step corresponds to a predetermined number of degrees. Thus, with each dose increment step, the dose setting knob is turned clock-wise an additional step corresponding to said predetermined number of degrees. So, in order to set a predetermined dose that corresponds to for instance two dose increment steps, the dose setting knob is turned clock-wise two steps. When the dose setting knob is rotated, the drive member 74 will rotate correspondingly, and hence also the one end of the drive spring attached to the drive member 74. The drive spring is hereby free to wind up and accumulate energy corresponding to the rotation of the spring tensioning means the number of degrees corresponding to one clock-wise step turn. Also the flexible arms 72 slide over the stop ledges 70.

The activation member comprises a ring-shaped member 82 where its distal end surface is provided with teeth 84 cooperating with the corresponding teeth 66 of the drive nut 58, FIG. 2. A return spring 86 is arranged between the proximal end surface of the ring-shaped member 82 of the activation member 80 and a distal end surface of a central annular wall 88, FIG. 5b, on the inner surface of the distal housing part 12 for urging the members in engagement with each other via the teeth 66, 84.

The device is intended to function as follows. A medicament container 14 is placed in the proximal housing part 10. The proximal part is then manually threaded into the guide shell 24. The guide shell 24 is prevented from rotating by the flexible tongues 42 in engagement with the ratchet 40. When the proximal housing part 10 is threaded into the distal housing part 12, the proximal end of the plunger rod 32 comes in contact with the distal stopper 34, whereby the distal stopper 34 is moved towards the proximal direction inside the medicament container. Further movement of the proximal housing part causes also the proximal stopper 35 to move whereby a passage is created between the chambers 36, 38 so that they communicate with each other, thereby causing a mixing of the medicament and the diluent. The movement of the proximal housing part is locked when the ridges 56 on the proximal housing part fit into the grooves 54 of the locking member 46.

When a dose is to be delivered the dose setting knob 76 is rotated, whereby the drive member 74 also is rotated. This rotation causes the torsion drive spring 78 to be tensioned. During rotation, the flexible arms 72 move out of contact with the stop ledges 70 of the ring-shaped part 68 of the drive nut 58 until they are moved in contact with subsequent stop ledges 70. The drive member 74 is prevented from being rotated back because the contact of the flexible arms 72 with the stop ledges 70.

Further, the drive nut 58 is in its turn prevented from rotating because the teeth 66 of the drive nut are in contact with the teeth 84 of the activation member. The dose setting knob 76 is rotated until a desired dose is set.

The user now positions the medicament delivery device at the delivery site and manually activates the medicament delivery device by sliding the activation member 80 against the force of the return spring 86. This causes the teeth 84 of the activation member 80 to move out of contact with the teeth 66 of the drive nut 58. Due to the power accumulated in the drive spring, the drive member 74 is now free to rotate by the force of the torsion drive spring 78, and because of the connection between the flexible arms 72 and the stop ledges 70, the drive nut 58 is also rotated.

Because of the rotation of the drive nut 58, which is in threaded engagement with the threads 62 of the plunger rod 32, and because of the rotational lock of the plunger rod 32 with the guide shell 24, the plunger rod 32 is axially advanced, which causes it to move the stoppers and to expel a dose of medicament.

The delivery device can now be removed from the delivery site. For subsequent delivery, a fresh delivery member is attached, if used, and the dose setting knob 76 is rotated to set the dose and tension the torsion drive spring 78. When the multi-dose container is empty and is to be replaced, the proximal housing part is manually rotated in the counter clockwise direction. In order to be able to do this, the locking member 46 has to be activated. This is done by pressing on the buttons 50 whereby the ring-shaped member 48 will flex in the radial direction such that the grooves 54 are moved out of contact with the ridges 56 of the proximal housing part 10. The proximal housing part 10 is now free to be rotated. However, because of the threaded connection with the guide shell 24, the latter is also rotated, which is allowed by the flexible tongues 42 sliding over the ratchet 40 in the counter clockwise direction. Because of the rotation of the guide shell 24, the plunger rod will also rotate, because of the rotational lock between the two components. Because the drive nut 58 now is locked from rotation because of its teeth 66 locking with the teeth 84 of the activation member, the plunger rod 32 is moved in the distal direction of the device until a circumferential ledge 90 on the plunger rod 32 comes in contact with the proximal surface of the end wall 26 of the guide shell 24. Further rotation of the proximal housing part 10 will now be in relation to the guide shell 24, whereby the proximal housing part 10 is threaded out of the guide shell 24 and the medicament container can now be removed and replaced with a new medicament container 14.

It is to be understood that the embodiment described above and shown in the drawings is to be regarded only as a non-limiting example of the invention band that it may be modified in many ways within the scope of the patent claims.

The invention claimed is:

1. A medicament delivery device, comprising:
a distal housing part;
a proximal housing part configured for a multi-chamber medicament container and movable in relation to the distal housing part for mixing at least two substances in the medicament container;
a plunger rod configured for acting on a distal stopper in the medicament container, wherein a relative movement of the distal and proximal housing parts toward each other forces the distal stopper against the plunger rod in a proximal direction for mixing the at least two substances;
a drive force unit configured for forcing the plunger rod in the proximal direction for subsequent delivery of medicament from the medicament container;
an activation member slidably arranged through the distal housing part and releasably connected to the drive force unit; and
a guide shell in the distal housing part and rotatable in only one direction, wherein the guide shell includes threads arranged to cooperate with corresponding threads on the proximal housing part, and the guide shell and the plunger rod include guide members such that the guide shell and plunger rod are rotationally locked but slidable in relation to each other;
wherein the drive force unit comprises:
a drive nut in threaded engagement with the plunger rod and releasably connected to the activation member;
a manually operated spring tensioning mechanism, comprising flexible locking tongues releasably connected to a ratchet of the drive nut for enabling rotational movement of the spring tensioning mechanism in only one direction in relation to the drive nut; and
a drive spring having one end connected to the spring tensioning mechanism and a second end connected to the distal housing part, such that when the spring tensioning mechanism is operated, the drive spring is locked in a tensioned state, and when the activation member is operated, the drive nut is released and thereby the drive spring is released from its tensioned state, whereby the plunger rod is moved in the proximal direction for delivery of medicament.

2. The medicament delivery device of claim 1, wherein the drive spring is a torsion drive spring.

3. A medicament delivery device, comprising:
a distal housing part;
a proximal housing part configured for a multi-chamber medicament container and movable in relation to the distal housing part for mixing at least two substances in the medicament container;
a plunger rod configured for acting on a distal stopper in the medicament container, wherein a relative movement of the distal and proximal housing parts toward each other forces the distal stopper against the plunger rod in a proximal direction for mixing the at least two substances;
a drive force unit configured for forcing the plunger rod in the proximal direction for subsequent delivery of medicament from the medicament container;
an activation member slidably arranged through the distal housing part and releasably connected to the drive force unit; and
a guide shell in the distal housing part and rotatable in only one direction, wherein the guide shell includes threads arranged to cooperate with corresponding threads on the proximal housing part, and the guide shell and the plunger rod include guide members such that the guide shell and plunger rod are rotationally locked but slidable in relation to each other;
wherein the guide shell is arranged with a longitudinally extending ratchet on its distal outer circumferential surface, the ratchet is arranged to cooperate with ledges provided on flexible tongues arranged on the distal housing part, and the ratchet and the ledges are configured such that the guide shell is rotatable in only one direction in relation to the distal housing part.

4. The medicament delivery device of claim 3, wherein the drive force unit comprises:
a drive nut in threaded engagement with the plunger rod and releasably connected to the activation member;
a manually operated spring tensioning mechanism, comprising flexible locking tongues releasably connected to a ratchet of the drive nut for enabling rotational movement of the spring tensioning mechanism in only one direction in relation to the drive nut; and
a drive spring having one end connected to the spring tensioning mechanism and a second end connected to the distal housing part, such that when the spring tensioning mechanism is operated, the drive spring is locked in a tensioned state, and when the activation member is operated, the drive nut is released and thereby the drive spring is released from its tensioned state, whereby the plunger rod is moved in the proximal direction for delivery of medicament.

5. The medicament delivery device of claim 4, wherein the drive spring is a torsion drive spring.

6. The medicament delivery device of claim 3, further comprising a proximal housing part locking member attached to the distal housing part, wherein the locking member is provided with a locking mechanism arranged to engage with a corresponding locking mechanism on the proximal housing part when the distal and proximal housing parts have reached a certain relative position after mixing, and when the medicament container is to be replaced with another, the proximal housing part locking member is activated to release the engagement between the locking mechanisms such that when a relative movement of the housing parts against each other also rotates the guide shell, whereby the plunger rod is moved in a distal direction to its initial position, and the proximal housing part is unscrewed from the distal housing part.

7. The medicament delivery device of claim 6, wherein the drive force unit comprises:
a drive nut in threaded engagement with the plunger rod and releasably connected to the activation member;
a manually operated spring tensioning mechanism, comprising flexible locking tongues releasably connected to a ratchet of the drive nut for enabling rotational movement of the spring tensioning mechanism in only one direction in relation to the drive nut; and
a drive spring having one end connected to the spring tensioning mechanism and a second end connected to the distal housing part, such that when the spring tensioning mechanism is operated, the drive spring is locked in a tensioned state, and when the activation member is operated, the drive nut is released and thereby the drive spring is released from its tensioned state, whereby the plunger rod is moved in the proximal direction for delivery of medicament.

8. The medicament delivery device of claim 7, wherein the drive spring is a torsion drive spring.

* * * * *